United States Patent

Browning et al.

[11] 3,973,760
[45] Aug. 10, 1976

[54] ULTRASONIC CLEANING AND STERILIZING APPARATUS

[75] Inventors: Iben Browning, Albuquerque, N. Mex.; Robert E. McClure, El Cerrito, Calif.

[73] Assignee: Robert E. McClure, El Cerrito, Calif.

[22] Filed: July 19, 1974

[21] Appl. No.: 489,964

[52] U.S. Cl. ............................. 259/72; 219/328; 310/8.7
[51] Int. Cl.² ............................. B01F 11/02
[58] Field of Search ............... 259/721, DIG. 41; 134/184, 1; 310/8.7; 219/328

[56] References Cited
UNITED STATES PATENTS

| | | | |
|---|---|---|---|
| 2,498,990 | 2/1950 | Fryklund | 310/8.7 X |
| 2,855,526 | 10/1958 | Jones | 310/8.5 |
| 3,720,402 | 3/1973 | Cummins | 259/72 |
| 3,851,861 | 12/1974 | Cummins | 259/72 |

*Primary Examiner*—Edward L. Roberts
*Attorney, Agent, or Firm*—Townsend and Townsend

[57] ABSTRACT

Apparatus for the ultrasonic cleaning and sterilization of soft contact lenses and fenestrated hard contact lenses at a temperature that is low relative to that of pasturization is disclosed. A transducer element is electrically connected to a source of oscillating current to produce mechanical oscillating motion. A capsule is provided which is adapted to contain a biologically inert solution in which the soft contact lenses are immersed and the capsule is then hermetically sealed but not pressurized. Apparatus is provided for demountably connecting the capsule to the transducer element so that a continuous spanwise mechanical coupling is provided from the transducer to this surface of the capsule. A tuner element may be interposed in the connecting apparatus. The lower surface of the capsule is vibrated at a preselected ultrasonic frequency to induce ultrasonic waves in the solution in the capsule and to heat the solution in a controlled manner to clean and sterilize the soft contact lenses therein. The solution in the capsule is sterilized as well, giving rise to alternative uses of the instant invention.

13 Claims, 4 Drawing Figures

ULTRASONIC CLEANING AND STERILIZING APPARATUS

BACKGROUND OF THE INVENTION

The present invention relates to apparatus for cleaning and sterilizing soft contact lenses and fenestrated hard contact lenses using ultrasonic waves in combination with controlled heating.

The use of hard contact lenses has been commonplace in spite of the difficulties associated with their use. Many persons wish to wear contact lenses for their aesthetic value, while others require contact lenses to correct vision problems which cannot be fully compensated for with normal glasses. These persons must suffer the discomfort associated with wearing the contact lenses, particularly in initially becoming accustomed to their use. Such lenses are often quite expensive, and many individuals, after purchasing the lenses, find that they cannot accustom themselves to their use and must return to regular glasses. Those persons who do wear contact lenses often have continuous eye irritation, particularly if the lenses are worn for too long at one time.

In order to avoid the discomforts associated with the wearing of hard contact lenses, soft contact lenses have been developed which can be worn in relative comfort. Some of the soft contact lenses currently available are constructed of a hydrophilic copolymer and include as much as 50% water absorbed by the copolymer. This structure provides a comfortable soft lens, but they are quite delicate and cannot ordinarily be heated to a sufficient degree or be treated with chemicals to sterilize them. Other soft contact lenses are hydrophobic and are also caustic to extreme heat and harsh chemicals. However, without sterilization, contamination of the eye with micro-organisms growing on or into the lens, such as Pseudomonas, might be able to cause infection or possibly damage of an eye. The Federal Food and Drug Administration recognizes this danger and requires that the wearers of contact lenses be furnished with means enabling them to sterilize the lenses on a daily basis. Since such sterilization procedures are now quite difficult, this limitation has seriously hampered the implementation of soft contact lenses and their availability for use by the general public.

It has therefore been proposed to sterilize soft contact lenses by subjecting them to ultrasonic waves as set forth in my corresponding application for "ULTRASONIC STERILIZATION METHOD AND APPARATUS," Ser. No. 388,848, now abandoned which is herein incorporated by reference. To be acceptable, lens sterilization by ultrasonic waves must be efficient, that is, it must be accomplished within a reasonable period of time by a device that operates overnight, for example, without requiring the attention of the user. The system must further be convenient so that the wearer of the contact lenses follows the recommended sterilization procedure and therefore properly sterilizes the lenses daily.

SUMMARY OF THE INVENTION

The present invention relates to apparatus for the ultrasonic cleaning and sterilization of soft contact lenses. A transducer element is electrically connected to a source of oscillating current to produce mechanical oscillating motion. A capsule is provided which is adapted to contain a solution in which the soft contact lenses are immersed. Apparatus are further provided for demountable connecting the capsule to the transducer element so that a continuous spanwise mechanical connection is provided from the transducer to the lower surface of the capsule. A tuner element may be interposed in the connecting apparatus. The lower surface of the capsule is vibrated at a preselected ultrasonic frequency to induce ultrasonic waves in the solution in the capsule which is heated in a controlled manner to clean and sterilize the soft contact lenses therein.

In order to provide a continuous spanwise mechanical connection between the removable capsule and the transducer, coupling is required (for example, by a fluid such as water or air). In the example of water as a coupling medium, a liquid receptacle is provided and partially filled with liquid. The capsule is inserted into the receptacle and locked therein, confining the liquid between the capsule and the receptacle. The base of the receptacle is either in contact with the tuner element or the transducer element itself forms the base of the receptacle so that a continuous spanwise mechanical coupling is provided from the transducer element to the capsule. Other coupling mechanisms which are substantially incompressible but easily deformable, such as molded rubber and, to a lesser degree air, can be used as well. The lower surface of the capsule is a thin membrane, and the coupling provided to this surface allows for the relatively efficient transmission of ultrasonic waves to the solution in the capsule to maximize the sterilization of the lenses without using excessive power while permitting the ready removal of the capsule from the apparatus. A cap is provided to cover the membranous lower surface of the capsule when the capsule is detached from the apparatus and consequently the capsule can also be used as a carrying case for the lenses, thereby greatly enhancing the convenience of wearing, handling, and maintaining the lenses.

The preferred embodiment of the present invention also includes a temperature sensing element or thermistor in thermal contact with the solution inside the capsule. The thermistor controls the amplitude of the oscillating current supplied to the transducer element and therefore the amplitude of the ultrasonic waves produced. As the temperature of the solution in the capsule increases, the amplitude of the ultrasonic waves will be reduced. Eventually, the heat induced by the ultrasonic waves and other sources such as the electronics will equal the heat lost to the environment and the system will become stabilized at a temperature which will not damage the lenses. In this manner, soft lenses can be conveniently placed in the capsule and mounted to the rest of the apparatus at night, the apparatus turned on and allowed to remain on until morning. When the soft contact lenses are taken out of the capsule in the morning, they will be cleaned and sterilized and ready for use without fear of infection. The convenience of the apparatus relative to those found in the art wil encourage its daily use by owners of soft contact lenses in accordance with FDA regulations, thus reducing the incidence of infection and other eye injury in soft contact lens wearers.

It will be noted that the cleaner-sterilizer of the present invention is equally advantageously used for cleaning and/or sterilizing hard contact lenses, particularly fenestrated hard contact lenses. Fenestrated lenses have a multitude of tiny holes to enhance the oxygen transfer to the cornea and to facilitate the tear flow.

The sterilization actually kills vegetative microorganisms on the lenses or in the surrounding fluid and doew not merely wash them off the lenses. Viruses and spores are unaffected by the sterilization, and its effect on protozoa has not been determined.

In case the lenses and their holder are not contained in the capsule, the fluid contained in the capsule is sterilized in the same fashion as is described in the teaching above. Any such fluid and the membranous bottom of the capsule and the coupling medium and any tuner element which is bonded to the ultrasonic transducer element and the transducer element itself, all act together to constitute one overall tuning element which responds to the input ultrasonic oscillation. This tuned set of elements determines the frequencies of oscillation which are resonant and an appropriate circuit can thereupon choose from among the various harmonics to which the system is resonant for the one which is maximally effective.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DESCRIPTION OF THE PREFERRED EMBODIMENT

Figure 1:
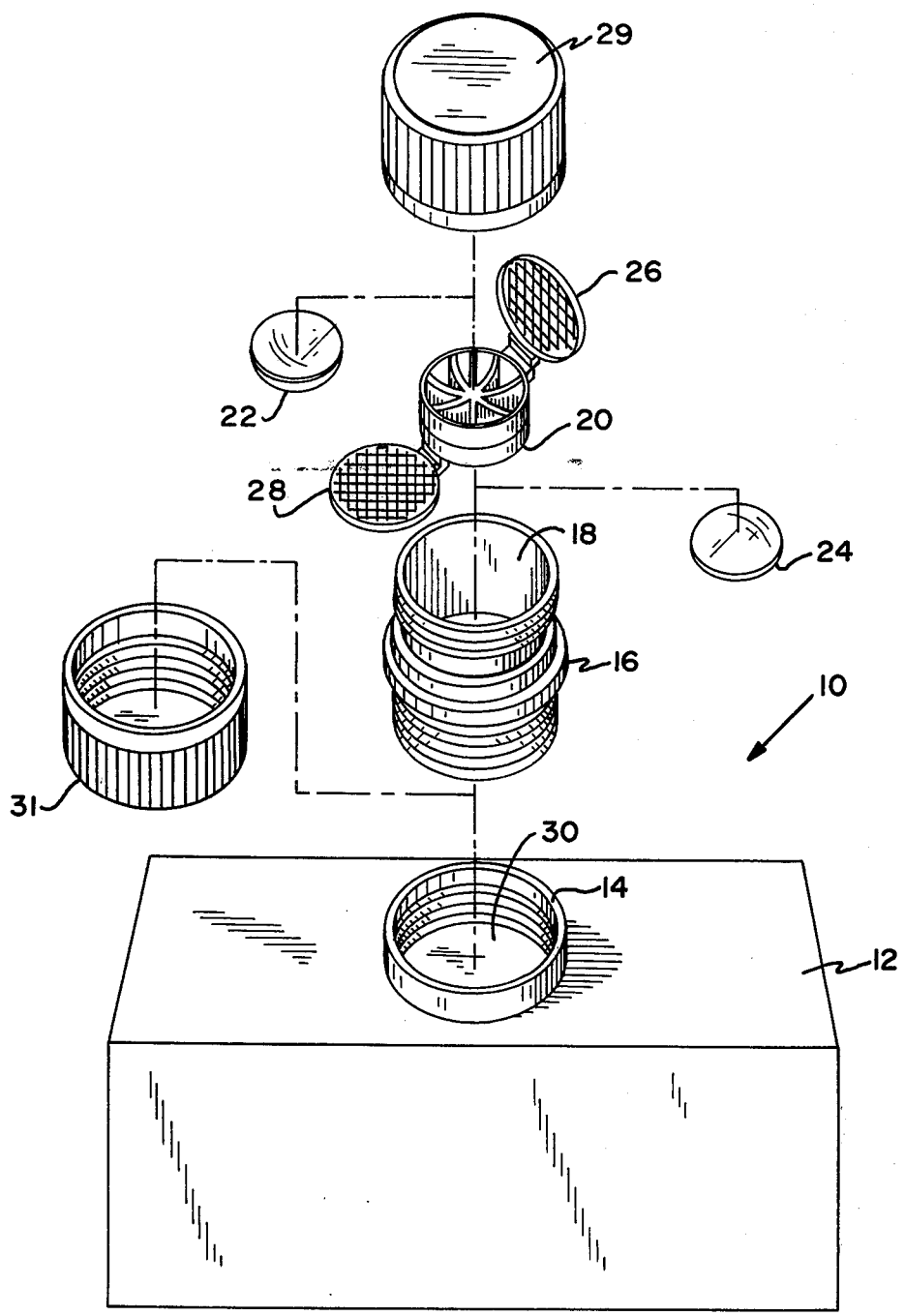
FIG. 1 is a perspective view of the apparatus of the present invention with the capsule portion thereof exploded.

The apparatus of the present invention is illustrated generally at 10 in FIG. 1. Apparatus 10 includes a case 12 containing the electronic and transducer components of the apparatus, which will be illustrated hereinafter, and an upwardly opening threaded receptacle 14. Receptacle 14 is adapted to be partially filled with a liquid, preferably distilled water to avoid the formation of unwanted deposits, prior to threadably engaging the receptacle with a capsule 16. Capsule 16 has interior volume 18 adapted to be filled with a saline solution. A lens holder 20 for soft, har, or fenestrated hard contact lenses 22, 24 is adapted to be immersed in the saline solution in capsule 16. Holder 20 has upper and lower chambers which can be closed by grates 26, 28 to secure lenses 22, 24 in the holder. Grates 26, 28 are readily open to fluid flow so that the saline solution in the interior volume 18 of the capsule 16 surrounds lenses 22, 24 and they are fully immersed in the solution.

When lenses 22, 24 have been placed in holder 20 and the holder has been placed in the solution in capsule 16, the capsule can be closed by engaging the upper end thereof with threaded cap 29. After closure of capsule 16, it can be engaged with receptacle 14.

The base of receptacle 14 comprises a mechanical tuning element 30 which will be illustrated in further detail hereinafter. The liquid in receptacle 14 will provide a continuous spanwise coupling medium between the lower surface of capsule 16 and the upper surface of tuning element 30. When tuning element 30 is vibrated mechanically, the vibrations will be transmitted directly through the liquid and to the lower surface of capsule 16 to induce ultrasonic waves in the solution in the capsule to clean and sterilize the lenses. When the lenses 22, 24 have been cleaned and sterilized, capsule 16 can be detached from casing 12 and used as a convenient carrying case for the lenses. In order to protect the thin membranous lower surface of capsule 16 through which the mechanical vibrations are transmitted, discussed in more detail hereinafter, a lower cap 31 can be threaded over the lower end of the capsule.

Figure 2:
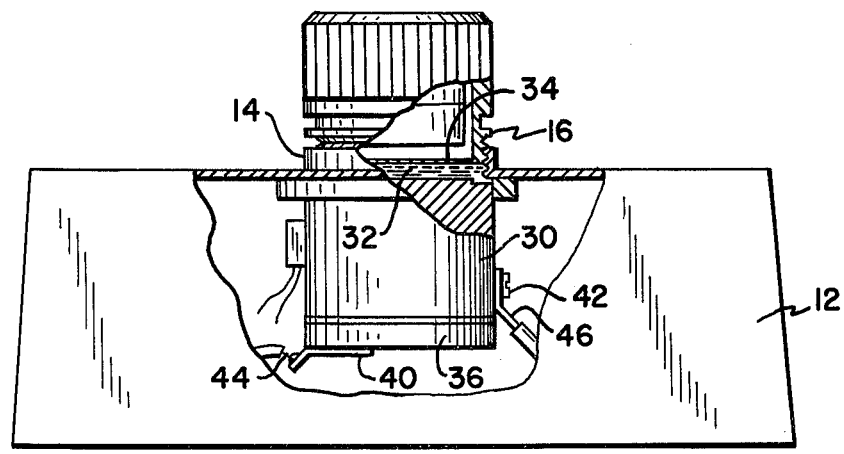
FIG. 2 is a side elevation view of the apparatus of the present invention partially cut away.
Figure 3:
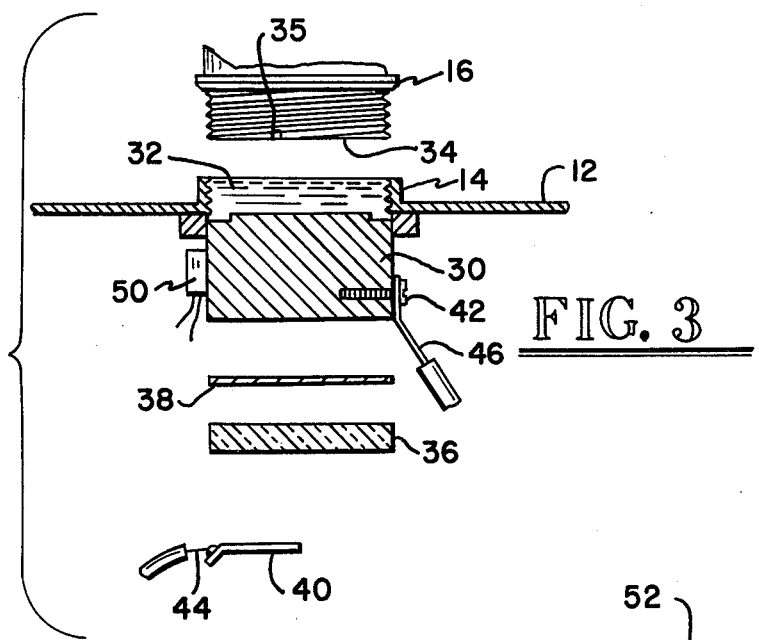
FIG. 3 is a fragmentary exploded view of the connecting apparatus of the present invention.

As is apparent from viewing FIGS. 2 and 3 in combination, attachment of capsule 16 to receptacle 14 will confine liquid 32 or other coupling medium between the lower surface 34 of capsule 16 and the upper surface of tuning element 30. Such coupling media should have the properties of being substantially imcompressible but easily deformable. One acceptable coupling medium is rubber with the air removed which is molded to receptacle 14 so that it is volumetrically confined when capsule 14 is in place. Air can also be used as the coupling medium, but since it is relatively compressible, the performance of the apparatus is degraded to a certain degree (approximately 15 more minutes are required for complete sterilization). In the embodiment illustrated, slot 35 allows for the escape of excess liquid so that capsule 16 is intimately coupled to receptacle 14. Thus, virtually the entire upper surface of tuning element 30 is mechanically coupled to the entire lower surface 34 of capsule 16 to transmit vibrations therebetween by way of coupling medium 32.

A cylindrical or thick disc transducer element 36 is disposed immediately beneath tuning element 30. Transducer element 36 is preferably a piezoelectric ceramic crystal, although other suitable transducer mechanisms could be employed. Crystal 36 is separated from tuning element 30 by an electrically conducting screen 38. Crystal 36 is glued or epoxied to the lower surface of tuning element 30 with electrically conducting screen 38 compressedly interposed therebetween so that electrical contact is maintained between the crystal and the tuning element.

Transducer element 36 is driven by applying an electric current to the upper and lower surfaces of the crystal. In order to promote electrical contact with the entire surface both upper and lower of crystal 36, the surfaces are coated with silver or a like conductor. A flat contact 40, for example, is simply glued or otherwise fixed to the lower surface of crystal 36 to apply oscillating current to that surface. To provide the oscillating current to the upper surface, an electrical connection 42 is made with metallic tuning element 30. Since screen 38 provides an electrical connection between tuning element 30 and crystal 36 over the entire upper surface of the crystal, an electrical connection is thus made from 42 to the upper surface of crystal 36. The oscillating current is applied through leads 44, 46 through contacts 40, 42, respectively, and thus to the upper and lower surfaces of crystal 36, with produces mechanical vibrations in response thereto.

The mechanical vibrations produced by crystal 36 are transmitted upwardly through tuning element 30.

Since a spanwise coupling is provided between the crystal and the tuning element over their respective widths, the entire width of the tuning element will serve as a transmitter for the mechanical vibrations. Correspondingly, such vibrations will be transmitted through coupling medium 32 to the lower surface 34 of capsule 16. The vibrations are transmitted through lower surface 34 to the solution inside capsule 16 to produce ultrasonic waves in the solution in the capsule. The lower surface 34 of capsule 16 is a thin membrane to minimize attenuation through the surface to the solution in the capsule.

The current supplied through leads 44, 46 oscillates at a selected ultrasonic frequency. The mechanical system including crystal 36, tuning element 30, coupling medium 32, and the fluid within capsule 16 is designed to resonate at such frequency, the size and weight of tuning element 30 being selected for this purpose. Furthermore, continuous spanwise mechanical coupling is provided from crystal 36 to capsule 16 to minimise losses of the mechanical energy. In this manner, the efficiency of the entire system is maximized, reducing the power required to operate the system so that excessive electricity is not wasted in its operation.

Figure 4:
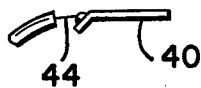
FIG. 4 is a schematic view of the thermal control unit of the present invention.

Since tuning element 30 is connected to capsule 16 by means of coupling medium 32, the temperature of the solution inside the capsule will be in direct proportion to the temperature of the tuning element. A thermistor 50 is mounted to the side of tuning element 30, and the electrical resistance of the thermistor is so chosen as to be sensitively proportional to the temperature of the tuning element. As illustrated in the schematic view of FIG. 4, the output of thermistor 50 is supplied to a power control unit 52 which controls the power to the oscillator 54 which drives crystal 36. Power control unit 52 and oscillator 54 are standard electronic components and are not discussed in detail herein.

The power supplied by power control 52 to oscillator 54 will determine the amplitude of the oscillating current produced and supplied to crystal 36. As the temperature of tuning element 30 increases in proportion to the temperature of the solution inside the capsule, power control unit 52 will decrease the power supplied to oscillator 54, thereby decreasing the amplitude of the oscillating current to crystal 36. As the amplitude of the electric current decreases and the temperature inside the solution increases, the system will eventually reach a stabilization point wherein the heat loss to the ambient air through the side walls of the capsule 16 and/or through vaporization will equal the heat input from the ultrasonic waves produced by crystal 36 and other sources. At this point, the power supplied to oscillator 54 will be constant and the temperature of the solution inside the capsule will also remain constant. As an alternative, the power supplied to oscillator 54 could be selectively intermittent, and the temperature maintained within an acceptable narrow range.

Power control unit 52 is designed so that the equilibrium temperature will be sufficiently low, usually in the order of about 50°C. so that the contact lenses will not sustain heat damage as is more fully set forth in the above referenced copending, commonly-owned patent application. This temperature is well below pasturization temperature (71°C.) which would be unacceptably high for most contact lenses.

In a series of tests performed with the apparatus of the present invention, the capsule was filled with a saline solution, and a sterile loop which has been placed in contact with a growing culture of Pseudomonas aeruginosa micro-organisms was then submerged in the fluid within the capsule. The capsule was then sealed with the cap and connected to the receptacle, which has been partially filled with distilled water to provide a mechanical connection at the bottom of the capsule. Different samples were tested for various lengths of time of operation of the ultrasonic apparatus, and the temperature was measured and the sterile loop was smeared onto a 7½ percent blood agar nutrient media. The smeared nutrient media was incubated at 96°F. for 24 hours to determine the resulting growth. The following results have been noted:

| | | |
|---|---|---|
| Control | 0 time | — luxuriant growth 25 degrees C |
| 1st sample | ½ hour | — luxuriant growth 38 degrees C |
| 2nd sample | 1 hour | — attenuated growth 46 degrees C |
| 3rd sample | 1½ hour | — severly attenuated 49 degrees C |
| 4th sample | 2 hours | — no growth 51 degrees C |
| 5th sample | 2½ hours | — no growth 50½ degrees C |
| 6th sample | 3 hours | — no growth 50½ degrees C |

As can be seen from the above table, a 2-hour operation of the ultrasonic apparatus appears to achieve complete biocidal action of the micro-organism tested. It should also be noted that the temperature of the solution in the capsule peaked at approximately 51°C. and then stabilized at 50.5°C. so that the temperature never reached a level at which the soft contact lenses could be damaged. Subsequent tests have indicated that acceptable sterilization is achieved at temperatures as low as 48°C., but a further reduction in temperature decreases the effectiveness of the system.

As can be seen from the above procedure, there is no sensitivity to the presence or absence of lenses 22, 24 or of the lens container 20. The fluid itself is sterilized and, for various purposes, this might be the objective for which such apparatus is used. For example, a possible use of the technique of the present invention may be the processing of blood plasma to kill bacteria without otherwise affecting the plasma. At the present state of the art, blood plasma is irradiated by ultraviolet to render the plasma shelf-stable. Such irradiation denatures organic material such as proteins in the plasma by causing mutations, while the present process results in a shelf-stable plasma without adversely affecting the plasma. As another example, the process of the present invention can be used as a substitute for pasturization of milk. Present medical techniques allow for the production of antibodies in milk by injecting the cow with antigens, and these antibodies convey passive immunity to drinkers of the milk. Such antibodies are denatured or destroyed by pasturization, but substantially unaffected by the sterilization process of the present invention.

While a preferred embodiment of the present invention has been illustrated in detail, it is apparent that modifications and adaptations of that embodiment will occur to those skilled in the art. For example, it is not essential that the capsule be threadably engaged with the receptacle, but other connective apparatus could be used as well, provided that a fluid coupling or other spanwise mechanical connection is provided between the capsule and the tuning element and/or crystal. It is to be expressly understood that this and other modifications of the preferred embodiment are within the spirit and scope of the present invention, as set forth in the following claims.

What I claim as new is:

1. Apparatus for the cleaning and sterilization of contact lenses, particularly soft or fenestrated hard contact lenses, said apparatus comprising:
   means for producing an oscillating current;
   transducer means electrically connected to the oscillating current producing means, said transducer means producing mechanical oscillating motion responsive to the oscillating current;
   a normally closed capsule adapted to contain a solution, the contact lenses being immersed in the solution in the capsule;
   means for demountably attaching the capsule to the transducer means and simultaneously defining an enclosed volume between the transducer means and the lower surface of the capsule; and
   a substantially incompressible, deformable coupling medium confined in and substantially completely filling the enclosed volume to provide a continuous spanwise mechanical coupling from the transducer means to the lower surface of the capsule to efficiently transmit ultrasonic waves from the transducer means to the solution in the capsule to clean and sterilize the contact lenses therein.

2. Apparatus as recited in claim 1 wherein said means for demountably attaching the capsule to the connecting means comprises means for threadably engaging the capsule with the connecting means.

3. Apparatus as recited in claim 1 wherein the lower surface of the capsule comprises a membrane to minimize attenuation of the mechanical oscillating motion at the lower surface of the capsule.

4. Apparatus for the cleaning and sterilization of contact lenses, particularly soft or fenestrated hard contact lenses, said apparatus comprising:
   means for producing an oscillating current at an ultrasonic frequency;
   a crystal electrically connected to the oscillating current producing means, said crystal producing mechanical vibrations responsive to the oscillating current;
   a tuning element overlying the crystal;
   an upwardly opening liquid receptacle overlying the tuning element, said receptacle containing a quantity of liquid; and
   a capsule demountably attachable to the liquid receptacle so that the liquid in said receptacle is confined between the capsule and the tuning element in spanwise contact with said capsule, said capsule containing a solution for immersion of the contact lenses therein, said crystal, tuning element, liquid and capsule in combination substantially resonating at the ultrasonic frequency of the oscillating current to produce ultrasonic waves in the solution in the capsule to efficiently cleanse and sterilize the contact lenses.

5. Apparatus as recited in claim 4 wherein the upper and lower surfaces of the tuning element and the lower surface of the capsule are substantially planar.

6. Apparatus as recited in claim 4 wherein the crystal comprises a piezoelectric ceramic element.

7. Apparatus as recited in claim 4 wherein the lower end of the liquid receptacle circumscribes the tuning element so that the upper surface of the tuning element is in direct spanwise contact with the quantity of liquid.

8. Apparatus for the cleaning and sterilization of contact lenses, particularly soft of fenestrated hard contact lenses, said apparatus comprising:
   an oscillator producing an oscillating current at an ultrasonic frequency;
   a piezoelectric ceramic element having a lower surface electrically connected to the oscillator;
   an electrically conducting screen overlying the crystal;
   a metallic tuning element overlying the conducting screen, said tuning element being secured to the crystal through the screen, said screen providing an electrical connection between the metallic element and the crystal, said tuning element being electrically connected to the oscillator to electrically connect the upper surface of the crystal thereto so that said crystal is producing mechanical vibrations responsive to the oscillating current;
   an upwardly opening liquid receptacle overlying the tuning element, the lower end of said receptacle circumscribing the upper surface of the tuning element, said receptacle containing a quantity of liquid;
   a capsule demountably attachable to the liquid receptacle so that the liquid in said receptacle is confined between the capsule and the upper surface of the tuning element in spanwise contact with said capsule and said tuning element, said capsule adapted to contain a solution for immersion of the contact lenses therein, said crystal, metallic tuning element, liquid and capsule in combination substantially resonating at the ultrasonic frequency of the oscillating current to produce ultrasonic waves in the solution in the capsule to efficiently cleanse and sterilize the contact lenses.

9. Apparatus for the cleaning and sterilization of contact lenses, particularly soft or fenestrated hard contact lenses, said apparatus comprising:
   means for producing mechanical oscillating motion at an ultrasonic frequency;
   a normally closed capsule adapted to contain a solution, the contact lenses adapted to be immersed in the solution in the capsule, one surface of the capsule comprising a thin membrane;
   means for mounting the capsule adjacent the oscillating motion producing means so that the surface thereof comprising a membran faces the oscillating motion producing means, said mounting means including means for defining a fluid tight volume between the membrane and the oscillating motion producing means; and
   a liquid completely filling the volume between the membrane and the oscillating motion producing means for efficient transmission of ultrasonic waves from the oscillating motion producing means through the membrane to the solution inside the capsule to clean and sterilize the contact lenses therein.

10. Apparatus as recited in claim 9 wherein the mounting means comprises an upwardly opening liquid receptacle overlying the oscillating motion producing means, the lower end of said liquid receptacle circumscribing the upper end of the oscillating motion producing means.

11. Apparatus as recited in claim 10 wherein the capsule is threadably engageable with the liquid receptacle.

12. Apparatus as recited in claim 1 wherein the coupling medium is a liquid.

13. Apparatus as recited in claim 1 wherein the coupling medium is water.

* * * * *